(12) United States Patent
Jiang et al.

(10) Patent No.: US 12,352,752 B2
(45) Date of Patent: Jul. 8, 2025

(54) APPLICATION OF NIEMANN-PICK C1 PROTEIN IN DIAGNOSIS AND TREATMENT OF CANCER

(71) Applicants: ACADEMY OF MILITARY MEDICAL SCIENCES, Beijing (CN); BEIJING PROTEOME RESEARCH CENTER, Beijing (CN)

(72) Inventors: Ying Jiang, Beijing (CN); Aihua Sun, Beijing (CN); Fuchu He, Beijing (CN); Chaoying Li, Beijing (CN); Jinan Zhou, Beijing (CN); Handong Wei, Beijing (CN)

(73) Assignees: ACADEMY OF MILITARY MEDICAL SCIENCES, Beijing (CN); BEIJING PROTEOME RESEARCH CENTER, Beijing (CN)

(*) Notice: Subject to any disclaimer, the term of this patent is extended or adjusted under 35 U.S.C. 154(b) by 1158 days.

(21) Appl. No.: 17/252,050

(22) PCT Filed: Dec. 10, 2018

(86) PCT No.: PCT/CN2018/120034
§ 371 (c)(1),
(2) Date: Dec. 14, 2020

(87) PCT Pub. No.: WO2019/237688
PCT Pub. Date: Dec. 19, 2019

(65) Prior Publication Data
US 2021/0263039 A1 Aug. 26, 2021

(30) Foreign Application Priority Data
Jun. 14, 2018 (CN) .......................... 201810612945.7

(51) Int. Cl.
| | | |
|---|---|---|
| G01N 33/574 | (2006.01) | |
| A61K 31/566 | (2006.01) | |
| A61K 31/7105 | (2006.01) | |
| A61K 45/06 | (2006.01) | |
| A61P 35/00 | (2006.01) | |
| C12Q 1/6886 | (2018.01) | |

(52) U.S. Cl.
CPC ..... G01N 33/57492 (2013.01); A61K 31/566 (2013.01); A61K 31/7105 (2013.01); A61K 45/06 (2013.01); A61P 35/00 (2018.01); C12Q 1/6886 (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 7,045,675 B2 * | 5/2006 | Carstea | ................. | C07K 14/47 |
| | | | | 530/300 |
| 2010/0004190 A1 | 1/2010 | Chan et al. | | |
| 2018/0141999 A1 * | 5/2018 | Chandran | .............. | A61K 39/00 |

FOREIGN PATENT DOCUMENTS

| | | |
|---|---|---|
| CN | 1852974 A | 10/2006 |
| CN | 102498404 A | 6/2012 |
| CN | 103596570 A | 2/2014 |
| CN | 103642927 A | 3/2014 |

OTHER PUBLICATIONS

Cote et al. (Nature 2011, 477, 344-348) (Year: 2012).*
Chen et al. Journal of Cancer vol. 9, pp. 556-563 (Year: 2018).*
Davies et al. Genomics 65, 137-145 (Year: 2000).*
O'Neill et al. Cancers 14, 3543, pp. 1-20 (Year: 2022).*
Naren et al. Leukemia Research 42, 59-67 (Year: 2016).*
Abcam, abcam.com Anti-Niemann Pick C1 antibody AB55706, pp. 1-2, retrieved on-line Feb. 20, 2024, https://www.abcam.com/products/primary-antibodies/niemann-pick-c1-antibody-ab55706.html (Year: 2024).*
Elisa Cleveland Clinic, pp. 1-8, retrieved on-line https://my.clevelandclinic.org/health/articles/24990-elisa#How%20Does%20The%20Elisa%20Technique%20Work?, Jul. 2, 2024 (Year: 2023).*
Mybiosource Niemann-Pick disease, type C1 (NPC 1), Elisa kit, pp. 1-6, retrieved on-line Jul. 2, 2024, https://www.mybiosource.com/npc1-human-elisa-kits/niemann-pick-disease-type-c1/9320668 (Year: 2024).*
International Search Report issued in corresponding International Application No. PCT/CN2018/120034; mailed Jan. 24, 2019; State Intellectual Property Office of the P.R. China, Beijing, China, 9 pgs.
First Office Action issued in corresponding Chinese Application No. 201810612945.7; mailed Jun. 12, 2020; State Intellectual Property Office of the P.R. China, Beijing, China, 11 pgs.
Second Office Action issued in corresponding Chinese Application No. 201810612945.7; mailed Dec. 2, 2020; State Intellectual Property Office of the P.R. China, Beijing, China, 10 pgs.
Wang et al.; "Expression and clinical significance of 3β-hydorxysteroid-Δ24 reductase in colorectal cancer"; Proceedings of the Third Military Medical University, Jun. 15, 2015, vol. 37, No. 11, pp. 1161-1165; Jun. 15, 2015.

* cited by examiner

*Primary Examiner* — Brian Whiteman
(74) *Attorney, Agent, or Firm* — HAUPTMAN HAM, LLP

(57) ABSTRACT

A use of Niemann-Pick C1 (NPC1) protein and a substance that inhibits NPC1 gene expression and/or protein activity, which is selected from at least one of the following (a)-(h): (a) for the preparation of kits for diagnosing cancer; (b) for the preparation of kits for predicting the prognosis of cancer; (c) for the preparation of kits for performing a companion diagnostic for cancer treatment; (d) for the preparation of drugs for the prevention and/or treatment of cancer; (e) for the preparation of drugs for the prevention and/or treatment of cancer spread and metastasis; (f) for the preparation of drugs for promoting apoptosis of cancer cells; (g) for the preparation of drugs for inhibiting cancer cells from developing into cancer; (h) for the preparation of drugs for inhibiting in vitro proliferation and growth of cancer cells.

4 Claims, 3 Drawing Sheets

Specification includes a Sequence Listing.

```
                        SEQUENCE LISTING

<160> NUMBER OF SEQ ID NOS: 1

<210> SEQ ID NO 1
<211> LENGTH: 59
<212> TYPE: DNA
<213> ORGANISM: Artificial sequence
<220> FEATURE:
<223> OTHER INFORMATION: Synthesized

<400> SEQUENCE: 1
ccggccacaa gttctatacc atattctcga gaatatggta tagaacttgt ggtttttg      59
```

APPLICATION OF NIEMANN-PICK C1 PROTEIN IN DIAGNOSIS AND TREATMENT OF CANCER

RELATED APPLICATIONS

The present application is a National Phase of International Application Number PCT/CN2018/120034 filed Dec. 10, 2018 and claims priority to Chinese Application Number 201810612945.7 filed Jun. 14, 2018.

INCORPORATION BY REFERENCE

The sequence listing provided in the file entitled Sequence_Listing_Mod_DNA.txt, which is an ASCII text file that was created on Dec. 10, 2020 and which comprises 358 bytes, is hereby incorporated by reference in its entirety.

TECHNICAL FIELD

The present invention belongs to the field of biomedicine, and relates to the application of Niemann-Pick C1 (NPC1) protein in the diagnosis and treatment of cancer.

BACKGROUND ART

The liver is the center of cholesterol metabolism in the body and plays a vital role in maintaining the balance of cholesterol metabolism in the body. The liver can produce large amounts of cholesterol by de novo synthesis. The blood cholesterol content is obviously positively correlated with the incidence of liver cancer. The level of cholesterol in cells is very important for cell growth, proliferation, differentiation and other life activities. Clinical studies have shown that serum cholesterol levels in patients with liver cancer are significantly reduced. However, the cholesterol level in liver cancer tissue is significantly higher than that in adjacent normal liver tissue. Niemann-Pick C1 (NPC1) protein is a transmembrane glycoprotein containing a sterol-sensing domain in intracellular lysosomes and late endosomes, which participates in endogenous cholesterol transport. It can monitor changes in cellular cholesterol levels. It is possible to adjust cellular lipid balance by changing the way of vesicle transport or directly participating in lipid transmembrane transport.

Hepatocellular carcinoma (HCC) is a malignant tumor with high morbidity and mortality. Every year, 55% of new and dead liver cancer patients worldwide occur in our country. The burden of liver cancer is heavy, and the 5-year survival rate is only about 10%. The main reason is that most of the patients with liver cancer are at an advanced stage when they are diagnosed and have lost the opportunity for surgery. However, even for small liver cancers smaller than 3 cm, some patients can survive for up to 10 or 20 years, while others die within one year and recur within a few months. Currently, the clinically commonly used diagnostic marker for liver cancer is alpha-fetoprotein (AFP). However, the sensitivity and specificity of AFP in the diagnosis of liver cancer are not ideal. Sorafenib, as a currently widely used targeted drug for liver cancer, can only effectively prolong the survival period of patients by 3 months. The diagnosis and treatment methods are very limited. Therefore, it is very important to find markers for early diagnosis of liver cancer and effective therapeutic targets for effective treatment of liver cancer.

SUMMARY OF THE INVENTION

The purpose of the present invention is to provide a novel use of a system for detecting the protein content or activity of Niemann-Pick C1 (NPC1) protein and a system for detecting the content or expression of NPC1 gene.

The use of a system for detecting the protein content or activity of Niemann-Pick C1 (NPC1) protein and a system for detecting the content or expression of NPC1 gene provided by the present invention is specifically for at least one of the following 1)-3): 1) preparation of products for screening or assisting in the diagnosis of cancer; 2) preparation of products for predicting the prognosis of cancer; 3) preparation of companion diagnostic products for cancer treatment.

The present invention also protects use of a system for detecting the content or activity of NPC1 protein alone and in combination with a system for detecting the content or activity of SOAT1 (cholesterol esterase) protein for at least one of the following 1)-3): 1) preparation of products for screening or assisting in the diagnosis of cancer; 2) preparation of products for predicting the prognosis of cancer; 3) preparation of companion diagnostic products for cancer treatment.

The present invention also protects use of a system for detecting the content or expression of NPC1 gene alone and in combination with a system for detecting the content or expression of SOAT1 (cholesterol esterase) gene for at least one of the following 1)-3): 1) preparation of products for screening or assisting in the diagnosis of cancer; 2) preparation of products for predicting the prognosis of cancer; 3) preparation of companion diagnostic products for cancer treatment.

In the above uses, the system for detecting the content or activity of NPC1 protein includes reagents and/or instruments required for detecting the content or activity of NPC1 protein.

The system for detecting the content or expression of NPC1 gene includes reagents and/or instruments required for detecting the content or expression of NPC1 gene.

The reagents required for detecting the content or expression of NPC1 gene include: primers that specifically amplify NPC1, or antibodies that specifically detect NPC1.

In the above uses, the system for detecting the content or activity of SOAT1 (cholesterol esterase) protein includes reagents and/or instruments required for detecting the content or activity of SOAT1 (cholesterol esterase) protein.

The system for detecting the content or expression of SOAT1 (cholesterol esterase) gene includes reagents and/or instruments required for detecting the content or expression of SOAT1 (cholesterol esterase) gene.

The reagents required for detecting the content or expression of SOAT1 (cholesterol esterase) gene include: primers that specifically amplify SOAT1 (cholesterol esterase), or antibodies that specifically detect SOAT1 (cholesterol esterase).

In the above uses, the sample used in the detection is blood (such as blood, serum, plasma) or tissue (such as liver tissue) from healthy people or patients with liver cirrhosis (LC) or hepatitis B or cancer (such as patients with hepatocellular carcinoma).

When blood is used as a test sample, enzyme-linked immunosorbent assay (ELISA) can usually be used to detect the concentration of NPC1 or SOAT1 in the blood.

When tissue is used as a test sample, immunohistochemistry can usually be used to detect the expression level of NPC1 or SOAT1 in the tissue.

In the above uses, the product can be a system, and the system can include reagents and/or instruments. The reagents include chips, preparations, kits or nucleic acid membrane strips. The kit can be a fluorescent quantitative PCR kit, an ELISA kit, an immunohistochemistry kit or others.

The present invention also protects a product. The product has at least one of the following uses: 1) screening or assisting in the diagnosis of cancer; 2) predicting the prognosis of cancer; 3) performing a companion diagnosis for cancer treatment.

The product provided by the present invention includes the system for detecting the content or activity of NPC1 protein or the system for detecting the content or expression of NPC1 gene.

Among them, the sample to be tested includes (but is not limited to) blood, serum, plasma and tissue biopsy.

In one embodiment, the substance used to detect the concentration of NPC1 protein is NPC1 protein antibody, specifically NPC1 antibody (Abcam, catalogue number: ab55706) used in immunohistochemistry and western blotting, or NPC1 kit (Mybiosource, catalogue number: MBS9320668) used in ELISA. Of course, it can also be other types of antibodies or other substances that can be used to detect the concentration of NPC1 protein.

The present invention also protects another product.

The product also has at least one of the following uses: 1) screening or assisting in the diagnosis of cancer; 2) predicting the prognosis of cancer; 3) performing a companion diagnosis for cancer treatment.

The product provided by the present invention includes the system for detecting the content or activity of NPC1 protein and the system for detecting the content or activity of SOAT1 (cholesterol esterase) protein; or the system for detecting the content or expression of NPC1 gene and the system for detecting the content or expression of SOAT1 (cholesterol esterase) gene.

The product can be a system, and the system can include reagents and/or instruments. The reagents include chips, preparations, kits or nucleic acid membrane strips. The kit can be a fluorescent quantitative PCR kit, an ELISA kit, an immunohistochemistry kit or others.

Use of a system with NPC1 as a marker for the preparation of products for screening or assisting in the diagnosis of cancer, the preparation of products for predicting the prognosis of cancer, or the preparation of products for companion diagnosis for cancer treatment also belong to the protection scope of the present invention.

Use of a system with NPC1 as a marker and a system with SOAT1 as a marker for the preparation of products for screening or assisting in the diagnosis of cancer, the preparation of products for predicting the prognosis of cancer, or the preparation of products for companion diagnosis for cancer treatment also belong to the protection scope of the present invention.

In the above uses, the product can be a system, and the system can include reagents and/or instruments. The reagents include chips, preparations, kits or nucleic acid membrane strips. The kit can be a fluorescent quantitative PCR kit, an ELISA kit, an immunohistochemistry kit or others.

Use of a system with NPC1 as a marker for screening or assisting in the diagnosis of cancer, for predicting the prognosis of cancer, or for performing a companion diagnosis for cancer treatment also belong to the protection scope of the present invention.

Use of a system with NPC1 as a marker and a system with SOAT1 as a marker for screening or assisting in the diagnosis of cancer, for predicting the prognosis of cancer, or for performing a companion diagnosis for cancer treatment also belong to the protection scope of the present invention.

Of course, NPC1 can be used in combination with SOAT1 as a marker to screen cancer or assist in the diagnosis of cancer or predict the prognosis of cancer or perform a companion diagnosis for cancer treatment and can also be used in combination with AFP (alpha-fetoprotein) or other proteins as a marker to screen cancer or assist in the diagnosis of cancer or predict the prognosis of cancer or perform a companion diagnosis for cancer treatment.

In the present invention, the screening or diagnosis object of the product is healthy people or patients with liver cirrhosis (LC) or cancer.

The present invention also protects a method for screening or assisting in the diagnosis of cancer or predicting the prognosis of cancer or as a companion diagnosis for cancer treatment.

The method comprises: detecting the content or expression of NPC1 in a sample of a subject to be tested, and diagnosing cancer or assisting in the diagnosis of cancer or predicting the prognosis of cancer or performing a companion diagnosis for cancer treatment based on the content or expression. Among them, the sample includes (but is not limited to) blood, serum, plasma and tissue biopsy.

The present invention also protects another method for screening or assisting in the diagnosis of cancer or predicting the prognosis of cancer or as a companion diagnosis for cancer treatment.

The method comprises: detecting the contents or expressions of NPC1 and SOAT1 in a sample of a subject to be tested, and screening or assisting in the diagnosis of cancer or predicting the prognosis of cancer or performing a companion diagnosis for cancer treatment based on the contents or expressions.

Among them, the sample includes (but is not limited to) blood, serum, plasma and tissue biopsy (such as liver biopsy).

The NPC1 protein is human NPC1 protein.

In the above uses, products or methods, the cancer includes solid cancer and non-solid cancer, including but not limited to hepatocellular carcinoma, cholangiocarcinoma, gastric cancer, pancreatic cancer, colon cancer, esophageal cancer, lung cancer, cervical cancer, ovarian cancer, breast cancer, prostate cancer, kidney cancer, bladder cancer, leukemia, cutaneous malignant melanoma.

Taking hepatocellular carcinoma as an example, experiments have shown that NPC1 protein can be used as a tumor marker for hepatocellular carcinoma (HCC). Based on the transcriptome data of 68 pairs of liver cancer tissues and the tissue chip data including 85 liver cancer patients' liver cancer tissues and adjacent normal liver tissues, the expression of NPC1 transcript and protein abundance in liver cancer tissue is significantly higher than that in adjacent normal liver tissue. In the serum of liver cancer patients, the abundance of NPC1 (mean: 7.12 ng/ml) is significantly higher than that of healthy control group (mean: 2.35 ng/ml), hepatitis B group (mean: 3.65 ng/ml) and liver cirrhosis group (mean: 4.31 ng/ml) ($P<0.01$). When healthy people are selected as screening objects, the threshold for determining HCC patients is serum NPC1 protein concentration >3.28 ng/ml (the sensitivity is 72% and the specificity is 93.75%). The area under the curve (AUC) when NPC1 alone is used as a marker for HCC screening is 0.87. When healthy people, people with hepatitis and people with liver cirrhosis are selected as screening objects, the threshold for determining HCC patients is serum NPC1 protein concentration >5.44 ng/ml (the sensitivity is 46% and the specificity is 92.86%). The area under the curve (AUC) is 0.75. It is suggested that NPC1 can be used as a marker to screen hepatocellular carcinoma from healthy people, people with hepatitis and people with liver cirrhosis.

Experiments have also proved that NPC1 protein can be used as a marker for hepatocellular carcinoma (HCC) prognostic evaluation. NPC1 is closely positively correlated with poor prognosis of liver cancer. The higher the abundance, the worse the patient prognosis (P=0.01).

Experiments have also proved that both NPC1 knockdown and inhibitor (U18666A) can significantly inhibit the proliferation and migration of liver cancer cells. It is suggested that NPC1 can be used as a marker for liver cancer screening and prognosis evaluation. Firstly, patients with liver cancer with higher malignancy are screened out using NPC1, and then NPC1 inhibitors are used for precise treatment. The NPC1 abundance has the function of screening or assisting in the diagnosis of cancer or predicting the prognosis of cancer or as a companion diagnosis for cancer treatment. The uses provided by the present invention uses the protein NPC1, whose expression is up-regulated both in the tissues and serum of patients with hepatocellular carcinoma, for the preparation of a diagnostic marker kit, or directly as a kit for diagnosing hepatocellular carcinoma, and protein NPC1 can also be used alone or in combination with other proteins for the preparation of a liver cancer diagnostic kit or the preparation of a prognosis kit or the preparation of a companion diagnostic kit for liver cancer treatment. It is suitable for clinical research and pathogenesis research of hepatocellular carcinoma in the fields of biology, medicine and pharmacy, and has wide practicability. Uses include, but are not limited to, various hepatocellular carcinoma related detection and research in the fields of biology, medicine and pharmacy.

The present invention also provides a new use of a substance that inhibits the gene expression and/or protein activity of Niemann-Pick C1 (NPC1) protein.

The use is selected from at least one of the following (a)-(e):
(a) for the preparation of drugs for the prevention and/or treatment of cancer;
(b) for the preparation of drugs for the prevention and/or treatment of cancer spread and metastasis;
(c) for the preparation of drugs for promoting apoptosis of cancer cells;
(d) for the preparation of drugs for inhibiting cancer cells from developing into cancer;
(e) for the preparation of drugs for inhibiting in vitro proliferation and growth of cancer cells.

The cancer includes solid cancer and non-solid cancer, including but not limited to hepatocellular carcinoma, cholangiocarcinoma, gastric cancer, pancreatic cancer, colon cancer, esophageal cancer, lung cancer, cervical cancer, ovarian cancer, breast cancer, prostate cancer, kidney cancer, bladder cancer, leukemia, cutaneous malignant melanoma.

The cancer cells include but are not limited to liver cancer cells, cholangiocarcinoma cells, gastric cancer cells, pancreatic cancer cells, colon cancer cells, esophageal cancer cells, lung cancer cells, cervical cancer cells, ovarian cancer cells, breast cancer cells, prostate cancer cells, renal cancer cells, bladder cancer cells, leukemia cells, cutaneous malignant melanoma cells.

The liver cancer cells can specifically be HepG2, PLC/PRF/5, Huh7 or MHCC97H cells.

The cervical cancer cells can specifically be Hela cell line, the colon cancer cells can specifically be a HCT116 cell line, the non-small cell lung cancer cells can specifically be a A549 cell line, the breast cancer cells can specifically be a MCF7 cell line, and the esophageal cancer cells can specifically be a ECA109 cell line and the leukemia cells can specifically be a Jurkat cell line.

The substance of the present invention that inhibits the gene expression and/or protein activity of Niemann-Pick C1 (NPC1) protein can be an inhibitory substance at the protein level, such as small molecule compounds or antibodies, or an inhibitory substance at the gene level, such as interfering RNA, CRISPR-CAS9 system, homologous recombination DNA fragments or vectors, etc. Small molecule compounds can inhibit NPC1 specifically or non-specifically.

In some specific embodiments of the present invention, the substance that inhibits the gene expression and/or protein activity of Niemann-Pick C1 (NPC1) protein can be an NPC1 inhibitor.

The NPC1 inhibitor can be specifically selected from: U18666A, or U18666A derivatives and analogs with the same effect, and compounds that also have the effect of inhibiting Niemann-Pick C1 protein.

The U18666A has a molecular formula of $C_{25}H_{41}NO_2 \cdot HCl$, CAS number: 3039-71-2, and a structural formula shown in formula I.

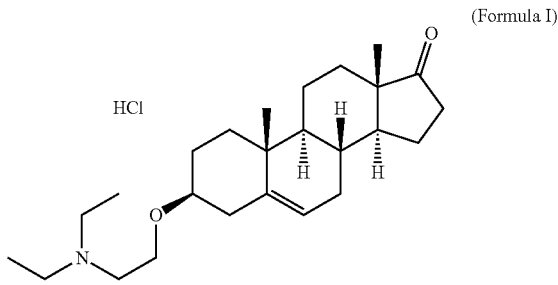

(Formula I)

The present invention also provides a pharmaceutical composition, which comprises a substance that inhibits the gene expression and/or protein activity of Niemann-Pick C1 (NPC1) protein as an active ingredient.

The pharmaceutical preparation should match the administration mode. The pharmaceutical composition of the present invention can be made into forms such as oral medicine and injection.

The pharmaceutical composition can also include additional anti-cancer drugs.

The anti-cancer drugs include chemotherapeutics, tumor antibodies and the like.

The anti-cancer drugs include (but are not limited to): adriamycin, vincristine, paclitaxel, cisplatin, carboplatin, 5-FU or a combination thereof.

The administration mode of the pharmaceutical composition is local administration or intratumoral administration.

The pharmaceutical composition has at least one of the following functions:
(a) for the prevention and/or treatment of cancer;
(b) for the prevention and/or treatment of cancer spread and metastasis;
(c) for promoting apoptosis of cancer cells;
(d) for inhibiting cancer cells from developing into cancer;
(e) for inhibiting in vitro proliferation and growth of cancer cells.

When necessary, one or more pharmaceutically acceptable carriers can be added to the pharmaceutical composition. The carrier includes conventional diluents, excipients, fillers, binders, wetting agents, disintegrants, absorption promoters, surfactants, adsorption carriers, lubricants and the like in the pharmaceutical field.

The drug can be made into injections, suspensions, powders, tablets, granules and other forms. The various dosage forms of drugs can be prepared according to conventional methods in the pharmaceutical field.

The present invention also provides an in vitro non-therapeutic method for inhibiting the growth of cancer cells, comprising:
(I) under the condition of adding Niemann-Pick C1 (NPC1) protein inhibitor, cultivating cancer cells, thereby inhibiting the growth of cancer cells; or
(I') reducing the expression of Niemann-Pick C1 (NPC1) gene or decreasing the protein amount or protein activity of Niemann-Pick C1 (NPC1) protein.

The cancer cells include but are not limited to liver cancer cells, cholangiocarcinoma cells, gastric cancer cells, pancreatic cancer cells, colon cancer cells, esophageal cancer cells, lung cancer cells, cervical cancer cells, ovarian cancer cells, breast cancer cells, prostate cancer cells, renal cancer cells, bladder cancer cells, leukemia cells, cutaneous malignant melanoma cells.

The present invention also provides a kit for treating cancer, which comprises the following components:
(a) a first therapeutic agent, which contains a substance that inhibits the gene expression and/or protein activity of Niemann-Pick C1 (NPC1) protein; in another preferred embodiment, the kit also comprises: (b) a second therapeutic agent, which is an anti-cancer drug containing an active ingredient different from the first therapeutic agent.

The kit provided by the present invention is used for the treatment of cancer, and the cancer includes solid cancer and non-solid cancer, including but not limited to liver cancer, cholangiocarcinoma, gastric cancer, pancreatic cancer, colon cancer, esophageal cancer, lung cancer, cervical cancer, ovarian cancer, breast cancer, prostate cancer, kidney cancer, bladder cancer, leukemia, cutaneous malignant melanoma. The liver cancer includes metastatic and non-metastatic liver cancer.

The present invention also provides a method for treating cancer, comprising the steps of: administering to a subject in need a substance that inhibits the gene expression and/or protein activity of Niemann-Pick C1 (NPC1) protein, or the pharmaceutical composition of the present invention.

The subject includes mammals, preferably humans.

The inventors of the present invention have proved through experiments that Niemann-Pick C1 (NPC1) protein is obviously highly expressed in liver cancer tissues, and its high abundance indicates that the prognosis of liver cancer patients is poor. Niemann-Pick C1 (NPC1) protein inhibitors can effectively inhibit the growth of human liver cancer and other tumor cells at the cellular and animal levels, and can be used as drug candidates for tumors, especially liver cancer.

It should be understood that, within the scope of the present invention, the above technical features and the technical features specifically described in the following (such as the examples) of the present invention can be combined with each other to form a new or preferred technical solution. Due to space limitations, they will not be described again.

DESCRIPTION OF THE DRAWINGS

Further to the general description provided above, FIG. 1A shows the transcriptome data of 68 pairs of liver cancer tissues (including 95 HCC tissue samples and 85 adjacent normal liver tissue samples);

FIG. 1B shows a representative plot of protein abundance expression of the NPC1 in tissue microarray hepatocellular carcinoma (T) and paired adjacent normal tissues (N);

FIG. 1C shows the NPC1 Statistical analysis of T/N protein abundance expression in tissue microarrays;

FIG. 1D shows the survival analysis of patients with high expression of NPC1 and low expression of NPC1 in the tissue chip;

FIG. 1E shows the survival analysis of patients with high expression of NPC1 and high expression of SOAT1 (cholesterol esterase) and other patients in the tissue chip.

FIG. 2A shows the determination of NPC1 expression in the serum of healthy people and patients with hepatitis, patients with liver cirrhosis and patients with liver cancer based on an ELISA kit;

FIG. 2B shows the ROC curve analysis of serum NPC1 protein levels between HCC and healthy populations;

FIG. 2C shows the ROC curve analysis of serum NPC1 protein levels among healthy population, hepatitis population and liver cirrhosis population.

FIG. 3A shows the effects of NPC1 knockdown on the proliferation of HepG2 and PLC/PRF/5 liver cancer cell lines;

FIG. 3B shows the effects of NPC1-specific inhibitor U18666A on the proliferation of HepG2, PLC/PRF/5, MHCC97H and Huh7 liver cancer cell lines.

FIG. 5A shows the list of tumors dissected after 23 days of treatment in the drug treatment group (U18666a, i.p., 20 mg/kg, once a day) and the control group;

FIG. 5B shows the statistical analysis of tumor weights of tumors dissected after 23 days of treatment in the drug treatment group (U18666a, i.p., 20 mg/kg, once a day) and the control group.

FIG. 6A shows that NPC1 knockdown and drug (U18666A) could reduce cholesterol on the surface of the plasma membrane based on the Filipin III-based cholesterol staining experiment results;

FIG. 6B shows that NPC1 inhibitor (U18666A) could increase the shedding of IL6R on the cell surface; and FIG. 6C shows that the activation of STAT3 signaling pathway is blocked after NPC1 knockdown or U18666A treatment.

DETAILED DESCRIPTION OF THE INVENTION

Figure 1:
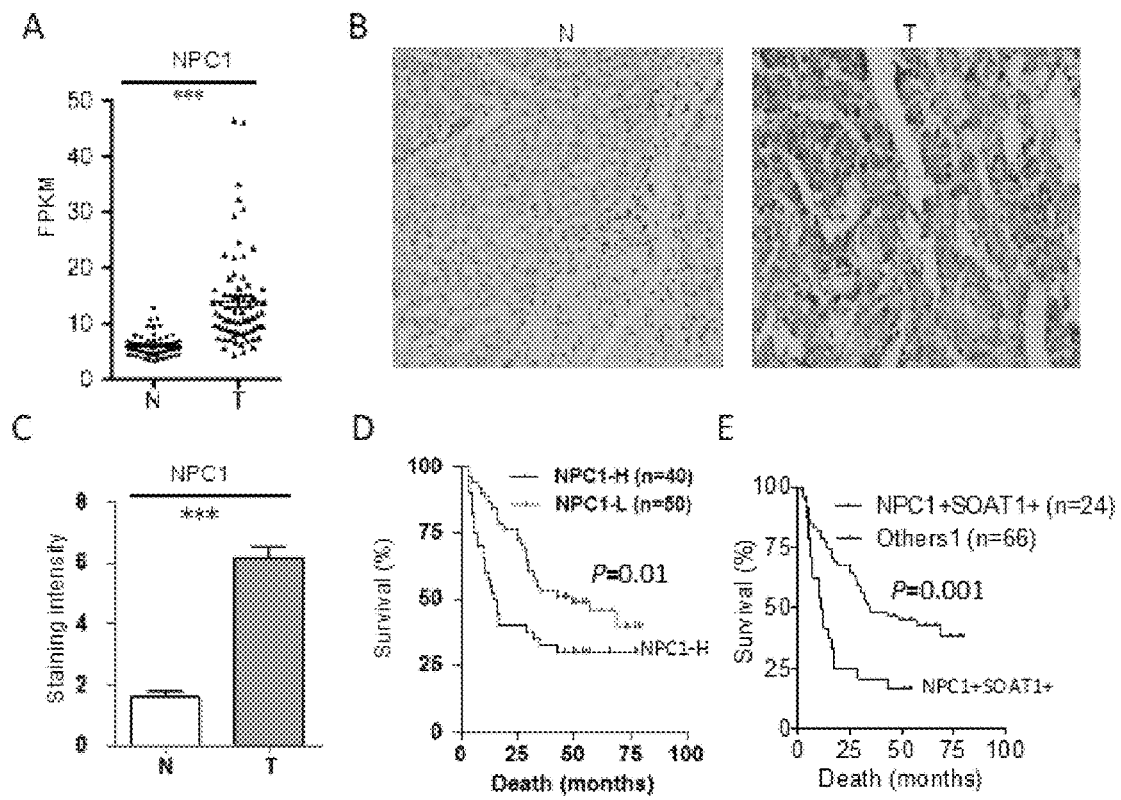
FIG. 1 shows that the expression of NPC1 is closely related to the occurrence and prognosis of liver cancer. Panel A: based on the transcriptome data of 68 pairs of liver cancer tissues and their paired adjacent normal liver tissues and the tissue chip data (including 95 HCC tissue samples and 85 adjacent normal liver tissue samples) (Panel B), it was found that the expression levels of NPC1 transcript and protein in liver cancer tissues were significantly higher than that in their paired adjacent normal liver tissues (Panels B and C). Panel D: survival analysis of patients with high expression of NPC1 and low expression of NPC1 in the tissue chip. The results showed that the overall survival of patients with high expression of NPC1 protein was significantly lower than that of patients with low expression of NPC1 (P=0.01). Panel E: survival analysis of patients with high expression of NPC1 and high expression of SOAT1 (cholesterol esterase) and other patients in the tissue chip. The results showed that it had a more significant relationship with the poor prognosis of liver cancer (P=0.001). It is suggested that NPC1 can be used alone or in combination with SOAT1 or other proteins to predict the prognosis of liver cancer. Unpaired Mann-Whitney test (Panels A and C), log-rank test (Panels D and E). *$P<0.05$, $P<0.01$, *$P<0.001$.

After extensive and in-depth research, the inventors of the present invention found for the first time that inhibiting the activity of NPC1 protein could effectively inhibit the growth of liver cancer at the cellular level and the animal level. The present invention has been completed on this basis.

Terms

NPC1

As used herein, the terms "NPC1" or "Niemann-Pick C1 protein" can be used interchangeably. Inhibiting the activity of NPC1 can effectively inhibit the growth of liver cancer at the cellular level. NPC1 can be used as a potential drug target for the treatment of liver cancer (especially advanced liver cancer). A person of ordinary skill in the art can use conventional methods to regulate the expression of NPC1 protein, reduce the expression of NPC1 or inactivate the expression of NPC1 gene (interruption inactivation, knockout, homologous recombination, interfering RNA, etc.). Methods of reducing the expression and activity of NPC1 protein include (but are not limited to) adding NPC1-specific inhibitors.

NPC1 Inhibitor

As used herein, the terms "NPC1 inhibitor" or "Niemann-Pick C1 protein inhibitor" can be used interchangeably, and both refer to compounds that have an inhibitory effect on the activity of NPC1 protein, such as U18666A, or U18666A derivatives and analogs with the same effect, and compounds that also have the effect of inhibiting Niemann-Pick C1 protein.

The present invention will be further explained below in combination with specific examples. It should be understood that these examples are only used to illustrate the present invention and not to limit the scope of the present invention. The experimental methods without specific conditions in the following examples usually follow the conventional conditions such as the conditions described in the Molecular Cloning: A Laboratory Manual (New York: Cold Spring Harbor Laboratory Press, 1989), or the conditions recommended by the manufacturer.

Materials and Methods

Reagents:
NPC1 antibody (ab55706) was purchased from Abcam;
NPC1 inhibitor U18666A was purchased from Santa;
Liver cancer tissue chip (HLiv-HCC180Sur-05): 95 hepatocellular carcinoma tissue samples in survival period: 95 hepatocellular carcinoma tissue samples/85 adjacent normal liver tissue samples. The operation time was from August 2006 to November 2009, and the follow-up time was 2013.9. The follow up time was 4-7 years. The chip was purchased from Shanghai Outdo Biotech Co., Ltd;
NPC1 ELISA reagent (MBS9320668) was purchased from Mybiosource;
Cell culture medium (DMEM) and fetal bovine serum were purchased from Invitrogen.

Cell Lines and Tissue Samples:
HepG2, PLC/PRF/5 and Huh7 cell lines were purchased from Union Cell Bank (Cell Center, Institute of Basic Medical Sciences, Chinese Academy of Medical Sciences & Peking Union Medical College);
MHCC97H cell line was purchased from the Liver Cancer Institute of Zhongshan Hospital, Fudan University;
Hela, HCT116, A549, MCF7, ECA109 and Jurkat cell lines were purchased from Cell Resource Center, Shanghai Institutes for Biological Sciences, Chinese Academy of Sciences.

The 120 serum samples used for serum ELISA were all from Zhongshan Hospital, Fudan University. Among them, 50 were liver cancer serum samples, 32 were normal human serum samples after physical examination, 19 were hepatitis B serum samples, and 19 were liver cirrhosis serum samples. All subjects were fasted for more than 8 hours before blood drawing, and about 5 ml of fasting venous blood was collected. After standing at room temperature for 30 minutes, the fasting venous blood was centrifuged at 3000 r/min for 10 minutes. Serum was collected and stored at −20° C. for NPC1 concentration monitoring.

Methods:

I. Transcriptome Data of 68 Pairs of Hepatocellular Carcinoma Tissue Samples and Paired Adjacent Normal Liver Tissue Samples Total RNA was extracted from liver tissue samples using TRIzol kit. The mRNA was enriched with Oligo (dT) magnetic beads, fragmentation buffer was added to the obtained mRNA to make the fragments into short fragments, and then the fragmented mRNA was used as a template to synthesize the first strand of cDNA with six-base random primers (random hexamers), and buffer, dNTPs, RNase H and DNA polymerase I were added to synthesize the second strand of cDNA. The product was purified by QiaQuick PCR kit and eluted with EB buffer. After performing end repair, adding base A and ligating a sequencing adapter, fragments with expected sizes were recovered by agarose gel electrophoresis and subject to PCR amplification to complete the entire library preparation work. The constructed library was sequenced on Illumina HiSeq2500. The whole experiment and the output data were handled by Novogene.

II. Detection of the Expression Difference of NPC1 in 95 HCC Tissue Samples and 85 Adjacent Normal Liver Tissue Samples by Immunohistochemistry:

1) Baking chip: put the tissue chip in an oven, adjust the temperature to 63'C, and bake the wax for one hour.
2) Dewaxing: after the chip is baked, take it out of the oven and put it into the automatic dyeing machine for dewaxing; the dewaxing process is as follows:
two cylinders of xylene, 15 minutes per cylinder (according to the time set by the instrument);
two cylinders of absolute ethanol, 7 minutes per cylinder (according to the time set by the instrument);
one cylinder of 90% alcohol, 5 minutes (according to the time set by the instrument); one cylinder of 80% alcohol, 5 minutes (according to the time set by the instrument);
3) One cylinder of 70% alcohol, 5 minutes (according to the time set by the instrument);
4) Antigen retrieval: take out the chip from the staining machine and rinse it with pure water 3 times, each time not less than 1 minute; during the rinsing process, put the citric acid repair solution or EDTA repair solution on the induction cooker and start heating.
5) Blocking: drop a commercial ready-to-use blocking agent on the chip and keep for 10-15 minutes.
6) Adding primary antibody at 1:20000: take out the chip, rinse with PBS buffer 3 times, once for 1 minute; take the primary antibody out of the refrigerator, centrifuge at 7200 rpm for not less than 30 seconds; dilute the primary antibody at a ratio of 1:2000 with antibody diluent and add the diluted primary antibody dropwise, and incubate at room temperature for 30 minutes.
7) Adding anti-rabbit secondary antibody: rinse the chip 3 times with PBS buffer, 1 minute each time; add the ready-to-use secondary antibody working solution dropwise, incubate at room temperature for 30 minutes; rinse with PBS 3 times after the time is up, each time not less than 1 minute.
8) DAB color development: take the DAB kit out of the refrigerator and prepare DAB according to 1 ml DAB diluent+1 drop of DAB chromogen; add the diluted DAB dropwise to the chip and observe the color development intensity for a maximum of 5 minutes, and then rinse under tap water for 5 minutes.
9) Hematoxylin counterstaining and mounting: add Harry's hematoxylin (SIGMA) dropwise to the chip for 1 minute, and after time is up, immerse it in 0.25% hydrochloric acid alcohol for not less than 2 seconds, rinse with tap water for more than 2 minutes, dry at room temperature and mount the chip.

III. Detection of the Concentration of NPC1 in Serum by Enzyme-Linked Immunosorbent Assay (ELISA)

Enzyme-linked immunosorbent assay (ELISA) was used to detect the concentration of NPC1 in serum samples. Three replicates were set for each group of serum samples, and the OD value was detected by a multifunctional microplate reader. The average of the three replicates was used as the final OD value of each group of samples. The expression levels of NPC1 in the liver cancer group, the normal group and the liver cirrhosis group were compared.

IV. NPC1 Knockdown

Knockdown vector: pLKO.1-TRC. The sequence of shRNA:

5'-CCGGCCACAAGTTCTATACCATATTCTCGAGAATATGGTATAGAAC

TTGTGGTTTTTTG-3' (as shown in SEQ ID NO: 1 in the

Sequence Listing)

1) On the first day, PLC/PRF/5 or HepG2 cells were seeded onto a 6-well plate.
2) On the second day, when the cell confluence was about 40-50%, NPC1-sh or NPC1-control lentivirus was added at 200 µl/well for virus infection.
3) On the third day, puromycin was added to infected PLC/PRF/5 or HepG2 cells to a final concentration of 2 µg/mL for selection.
4) On the sixth day, part of the cells was collected according to the conventional method for CCK8 experiment, and part of the cells were lysed to obtain proteins and subjected to Western blotting.

V. CCK8 Experiment

1) On the first day, after routine trypsinization and counting of cells in a 60 mm culture dish, the cells were seeded onto four 96-well plates at a density of 5000 cells/well.
2) On the second day, after about 24 hours of culture, the cell growth was in the logarithmic growth phase and the culture medium was replaced with a new culture medium with different concentrations of SOAT1 inhibitor in a volume of 100 µL/well. 10 µM group, 20 µM group and control group (1‰ DMSO) were set, each group included three repeated wells. 10% CCK8 (100 µL/well) was added to the wells of one 96-well plate, and OD value of 0 h was measured at 450 nm after 1 h, with cell-free wells as background.
3) On the third day, 10% CCK8 was added to the wells of one 96-well plate and OD value of 24 h was measured at 450 nm after 1 h.

4) On the fourth day, 10% CCK8 was added to the wells of one 96-well plate and OD value of 48 h was measured at 450 nm after 1 h.
5) On the fifth day, 10% CCK8 was added to the wells of the last 96-well plate and OD value of 72 h was measured at 450 nm after 1 h.
6) OD values at all time points were summarized and a growth curve was drawn.

VI. Western Blotting Detection

The conventional western blotting method was adopted.

VII. Statistical Analysis:

All analyses were done using GraphPad Prism software. P<0.05 was considered to indicate a significant difference.

Example 1. The High Expression of NPC1 in Liver Cancer is Closely Related to the Occurrence and Prognosis of Liver Cancer In order to confirm the high expression of NPC1 in liver cancer, the inventors of the present invention used the transcriptome data of 68 pairs of liver cancer tissue samples and their paired adjacent normal liver tissue samples to analyze the expression of NPC1 in liver cancer tissues and adjacent normal liver tissues, and found that NPC1 transcript was highly expressed in liver cancer tissue samples (FIG. 1, panel A). The inventors of the present invention used liver cancer tissue chip (95 HCC tissue samples and 85 adjacent normal liver tissue samples) to detect that NPC1 protein was significantly highly expressed in HCC (FIG. 1, panels B and C) and the overall survival of patients with high NPC1 expression was significantly lower than that of patients with low NPC1 expression (P=0.01) (FIG. 1, panel D). Survival analysis was performed for patients with both NPC1 and SOAT1 (cholesterol esterase) high expressions and other patients in the tissue chip (FIG. 1, panel E). The results showed that it had a more significant relationship with the poor prognosis of liver cancer (P=0.001). It is suggested that NPC1 can be used alone or in combination with SOAT1 or other proteins to predict the prognosis of liver cancer. Unpaired Mann-Whitney test (FIG. 1, panels A and C), log-rank test (FIG. 1, panels D and E). *P<0.05, P<0.01,*P<0.001.

Example 2. NPC1 is Significantly Increased in Liver Cancer Serum Samples

Figure 2:
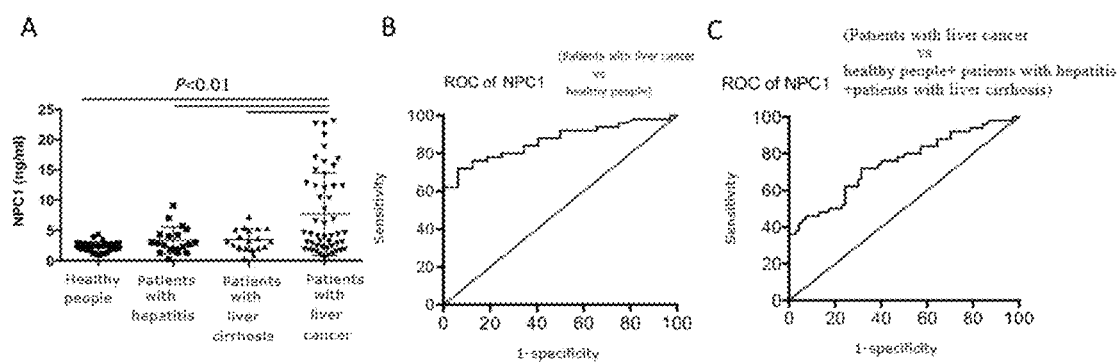
FIG. 2 shows the determination of NPC1 expression in the serum of healthy people and patients with hepatitis, patients with liver cirrhosis and patients with liver cancer based on an ELISA kit. The results showed that NPC1 was significantly elevated in the serum of patients with liver cancer (Panel A). It is suggested that NPC1 can be used as a diagnostic marker for screening liver cancer from healthy people, patients with hepatitis and patients with liver cirrhosis. The ROC curve analysis of serum NPC1 protein levels between HCC and healthy populations (Panel B) showed that NPC1 could be used as a potential marker for screening liver cancer from healthy population (AUC=0.87). The ROC curve analysis of serum NPC1 protein levels in HCC population and non-HCC mixed population (healthy population, hepatitis population and liver cirrhosis population) (Panel C) showed that NPC1 could be used as a potential marker for screening liver cancer from healthy and benign liver disease populations (AUC=0.75).

In order to confirm the high expression of NPC1 in liver cancer, the inventors of the present invention used human serum samples to detect the expression of NPC1 in different populations with an ELISA kit (FIG. 2).

ELISA results of NPC1 protein expression level in serum samples of liver cancer group, normal group, hepatitis group and liver cirrhosis group: in the serum of liver cancer patients, the abundance of NPC1 (mean: 7.12 ng/ml) was significantly higher than that of the healthy control group (mean: 2.35 ng/ml) and the hepatitis group (mean: 3.65 ng/ml) and the liver cirrhosis group (mean: 4.31 ng/ml) (P<0.01). A statistical analysis of the NPC1 protein content in each group of samples (unpaired Mann-Whitney test) found that serum NPC1 protein was significantly different in the liver cancer group and the normal group/hepatitis group/liver cirrhosis group (P<0.01) (FIG. 2, panel A). It is suggested that NPC1 can be used as a diagnostic marker for screening liver cancer from healthy people, people with liver cirrhosis and people with hepatitis.

When healthy people were selected as screening objects, the threshold for determining HCC patients was serum NPC1 protein concentration >3.28 ng/ml (the sensitivity was 72% and the specificity was 93.75%). The area under the curve (AUC) when NPC1 alone was used as a marker for HCC screening was 0.87 (FIG. 2, panel B). When healthy people, people with hepatitis and people with liver cirrhosis were selected as screening objects, the threshold for determining HCC patients was serum NPC1 protein concentration >5.44 ng/ml (the sensitivity was 46% and the specificity was 92.86%). The area under the curve (AUC) was 0.75 (FIG. 2, panel B), which was better than the AUC value (0.65-0.73) when AFP (alpha-fetoprotein) was used alone as reported in the literature (Luo, P. et al. A Large-scale, multicenter serum metabolite biomarker identification study for the early detection of hepatocellular carcinoma. Hepatology. 29561 (2017)). It is suggested that NPC1 can be used as a marker to screen hepatocellular carcinoma from healthy people, people with hepatitis and people with liver cirrhosis.

The concentration thresholds of the above two diagnoses were the thresholds corresponding to the maximum Youden indexes of the ROC curves, and the thresholds, sensitivities, 1-specificities and Youden indexes corresponding to the diagnoses of healthy people and HCC patients, non-HCC people (healthy people and patients with hepatitis B and patients with liver cirrhosis) and HCC patients are shown in Table 1 and Table 2 (the maximum Youden indexes and the corresponding thresholds are marked in bold).

TABLE 1

Thresholds, sensitivities, specificities and Youden indexes with healthy people as the control group

| Threshold | Sensitivity (%) | 1-specificity (%) | Youden index |
|---|---|---|---|
| 2.84 | 80.00 | 25.00 | 0.55 |
| 2.90 | 78.00 | 25.00 | 0.53 |
| 2.95 | 78.00 | 21.87 | 0.56 |
| 2.97 | 78.00 | 18.75 | 0.59 |
| 2.98 | 76.00 | 18.75 | 0.57 |
| 3.00 | 76.00 | 15.62 | 0.60 |
| 3.03 | 76.00 | 12.50 | 0.64 |
| 3.08 | 74.00 | 12.50 | 0.62 |
| 3.15 | 72.00 | 12.50 | 0.60 |
| 3.19 | 72.00 | 9.37 | 0.63 |
| 3.28 | 72.00 | 6.25 | 0.66 |
| 3.36 | 70.00 | 6.25 | 0.64 |
| 3.41 | 68.00 | 6.25 | 0.62 |
| 3.55 | 66.00 | 6.25 | 0.60 |
| 3.69 | 64.00 | 6.25 | 0.58 |
| 3.85 | 62.00 | 6.25 | 0.56 |
| 3.97 | 62.00 | 3.12 | 0.59 |
| 4.05 | 62.00 | 0.00 | 0.62 |
| 4.11 | 60.00 | 0.00 | 0.60 |
| 4.13 | 58.00 | 0.00 | 0.58 |
| 4.15 | 56.00 | 0.00 | 0.56 |
| 4.21 | 54.00 | 0.00 | 0.54 |
| 4.33 | 52.00 | 0.00 | 0.52 |
| 4.55 | 50.00 | 0.00 | 0.50 |
| 4.84 | 48.00 | 0.00 | 0.48 |
| 5.21 | 46.00 | 0.00 | 0.46 |
| 5.63 | 44.00 | 0.00 | 0.44 |
| 6.11 | 42.00 | 0.00 | 0.42 |
| 6.48 | 40.00 | 0.00 | 0.40 |
| 7.21 | 38.00 | 0.00 | 0.38 |
| 8.80 | 36.00 | 0.00 | 0.36 |
| 9.81 | 34.00 | 0.00 | 0.34 |
| 10.00 | 32.00 | 0.00 | 0.32 |
| 10.29 | 30.00 | 0.00 | 0.30 |
| 10.55 | 28.00 | 0.00 | 0.28 |
| 10.90 | 26.00 | 0.00 | 0.26 |
| 11.17 | 24.00 | 0.00 | 0.24 |
| 11.65 | 22.00 | 0.00 | 0.22 |
| 12.44 | 20.00 | 0.00 | 0.20 |
| 12.99 | 18.00 | 0.00 | 0.18 |

TABLE 1-continued

Thresholds, sensitivities, specificities and Youden indexes with healthy people as the control group

| Threshold | Sensitivity (%) | 1-specificity (%) | Youden index |
|---|---|---|---|
| 13.42 | 16.00 | 0.00 | 0.16 |
| 14.50 | 14.00 | 0.00 | 0.14 |
| 15.47 | 12.00 | 0.00 | 0.12 |
| 15.60 | 10.00 | 0.00 | 0.10 |
| 15.72 | 8.00 | 0.00 | 0.08 |
| 15.97 | 6.00 | 0.00 | 0.06 |
| 16.70 | 4.00 | 0.00 | 0.04 |
| 17.49 | 2.00 | 0.00 | 0.02 |

TABLE 2

Thresholds, sensitivities, specificities and Youden indexes with non-HCC people (healthy people and patients with hepatitis B and patients with liver cirrhosis) as the control group

| Threshold | Sensitivity (%) | 1-specificity (%) | Youden index |
|---|---|---|---|
| 1.31 | 100.00 | 98.57 | 1.43 |
| 1.32 | 100.00 | 97.14 | 2.86 |
| 1.37 | 98.00 | 97.14 | 0.86 |
| 1.45 | 98.00 | 95.71 | 2.29 |
| ... | ... | ... | ... |
| ... | ... | ... | ... |
| ... | ... | ... | ... |
| ... | ... | ... | ... |
| ... | ... | ... | ... |
| 3.41 | 68.00 | 31.43 | 36.57 |
| 3.49 | 66.00 | 31.43 | 34.57 |
| 3.58 | 66.00 | 30.00 | 36.00 |
| 3.69 | 64.00 | 30.00 | 34.00 |
| 3.75 | 62.00 | 30.00 | 32.00 |
| 3.85 | 62.00 | 28.57 | 33.43 |
| 3.97 | 62.00 | 27.14 | 34.86 |
| 3.99 | 62.00 | 25.71 | 36.29 |
| 4.05 | 62.00 | 24.29 | 37.71 |
| 4.11 | 60.00 | 24.29 | 35.71 |
| 4.13 | 58.00 | 24.29 | 33.71 |
| 4.15 | 56.00 | 24.29 | 31.71 |
| 4.21 | 54.00 | 24.29 | 29.71 |
| 4.31 | 52.00 | 24.29 | 27.71 |
| 4.36 | 52.00 | 22.86 | 29.14 |
| 4.43 | 50.00 | 22.86 | 27.14 |
| 4.49 | 50.00 | 21.43 | 28.57 |
| 4.50 | 50.00 | 20.00 | 30.00 |
| 4.58 | 50.00 | 18.57 | 31.43 |
| 4.69 | 50.00 | 17.14 | 32.86 |
| 4.76 | 48.00 | 17.14 | 30.86 |
| 4.82 | 48.00 | 15.71 | 32.29 |
| 4.85 | 48.00 | 14.29 | 33.71 |
| 4.92 | 48.00 | 12.86 | 35.14 |
| 4.98 | 46.00 | 12.86 | 33.14 |
| 5.08 | 46.00 | 11.43 | 34.57 |
| 5.20 | 46.00 | 10.00 | 36.00 |
| 5.34 | 46.00 | 8.57 | 37.43 |
| 5.44 | 46.00 | 7.14 | 38.86 |
| 5.48 | 44.00 | 7.14 | 36.86 |
| 5.66 | 44.00 | 5.71 | 38.29 |
| 5.98 | 42.00 | 5.71 | 36.29 |
| 6.29 | 42.00 | 4.29 | 37.71 |
| 6.48 | 40.00 | 4.29 | 35.71 |
| 6.80 | 38.00 | 4.29 | 33.71 |
| 7.47 | 38.00 | 2.86 | 35.14 |
| 8.09 | 36.00 | 2.86 | 33.14 |
| 8.90 | 36.00 | 1.43 | 34.57 |

TABLE 2-continued

Thresholds, sensitivities, specificities and Youden indexes with non-HCC people (healthy people and patients with hepatitis B and patients with liver cirrhosis) as the control group

| Threshold | Sensitivity (%) | 1-specificity (%) | Youden index |
|---|---|---|---|
| 9.61 | 36.00 | 0.00 | 36.00 |
| 9.81 | 34.00 | 0.00 | 34.00 |
| 10.00 | 32.00 | 0.00 | 32.00 |
| 10.29 | 30.00 | 0.00 | 30.00 |
| 10.55 | 28.00 | 0.00 | 28.00 |
| ... | ... | ... | ... |
| ... | ... | ... | ... |
| ... | ... | ... | ... |
| 16.70 | 4.00 | 0.00 | 4.00 |
| 17.49 | 2.00 | 0.00 | 2.00 |

Figure 3:
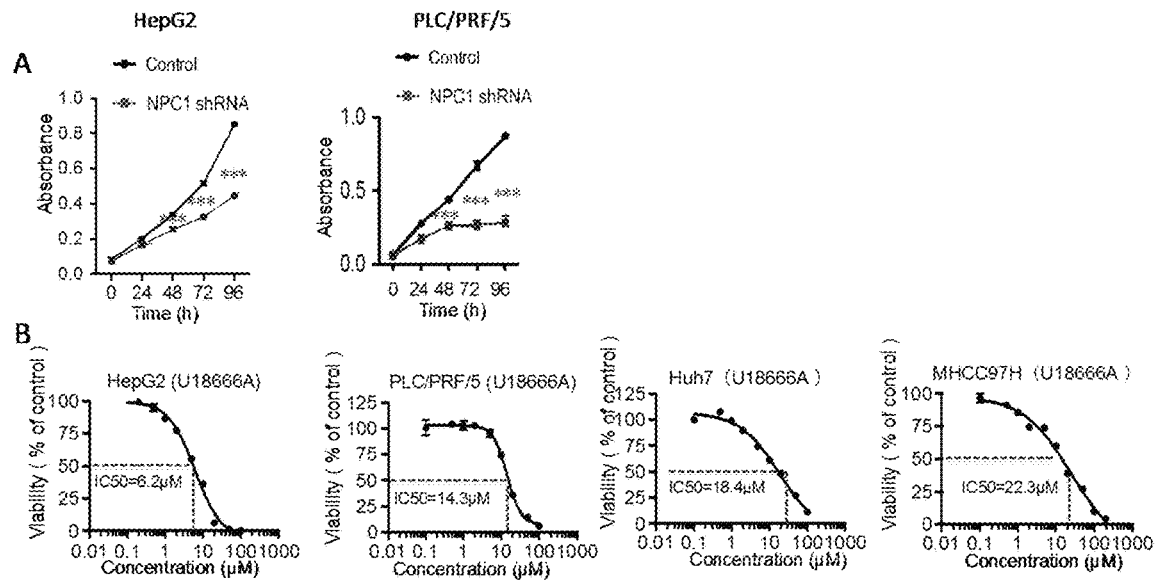
FIG. 3 shows the detection of the effects of NPC1 knockdown and inhibitor U18666A on the proliferation of liver cancer cell lines. Panel A shows the effects of NPC1 knockdown on the proliferation of HepG2 and PLC/PRF/5 liver cancer cell lines; Panel B shows the effects of NPC1-specific inhibitor U18666A on the proliferation of HepG2, PLC/PRF/5, MHCC97H and Huh7 liver cancer cell lines. The results suggest that targeting NPC1 can significantly inhibit the proliferation of liver cancer cell lines. NPC1 can be used as a target for liver cancer treatment. Patients with higher malignant liver cancer screened by NPC1 can be subjected to a precise treatment targeting NPC1. Unpaired Mann-Whitney test, *$P<0.05$, $P<0.01$, *$P<0.001$.

Example 3. Both NPC1 Knockdown and Inhibitor can Inhibit the Growth of Liver Cancer Cells In this example, the inventors of the present invention studied the effects of NPC1 shRNA and inhibitor in inhibiting the growth of liver cancer cells. The results showed that both NPC1 knockdown and inhibitor U18666A could significantly inhibit the proliferation of liver cancer cells (HepG, PLC/PRF/5, MHCC97H and Huh7 cells) (FIG. 3). This shows that targeting NPC1 can significantly inhibit the proliferation of liver cancer cell lines, suggesting that NPC1 can be used as a target for the treatment of liver cancer.

Example 4. NPC1 Inhibitor can Inhibit the Growth of Cancer Cells

In this example, the inventors of the present invention studied the role of NPC1 inhibitor in the growth of common cancer cells.

Figure 4:
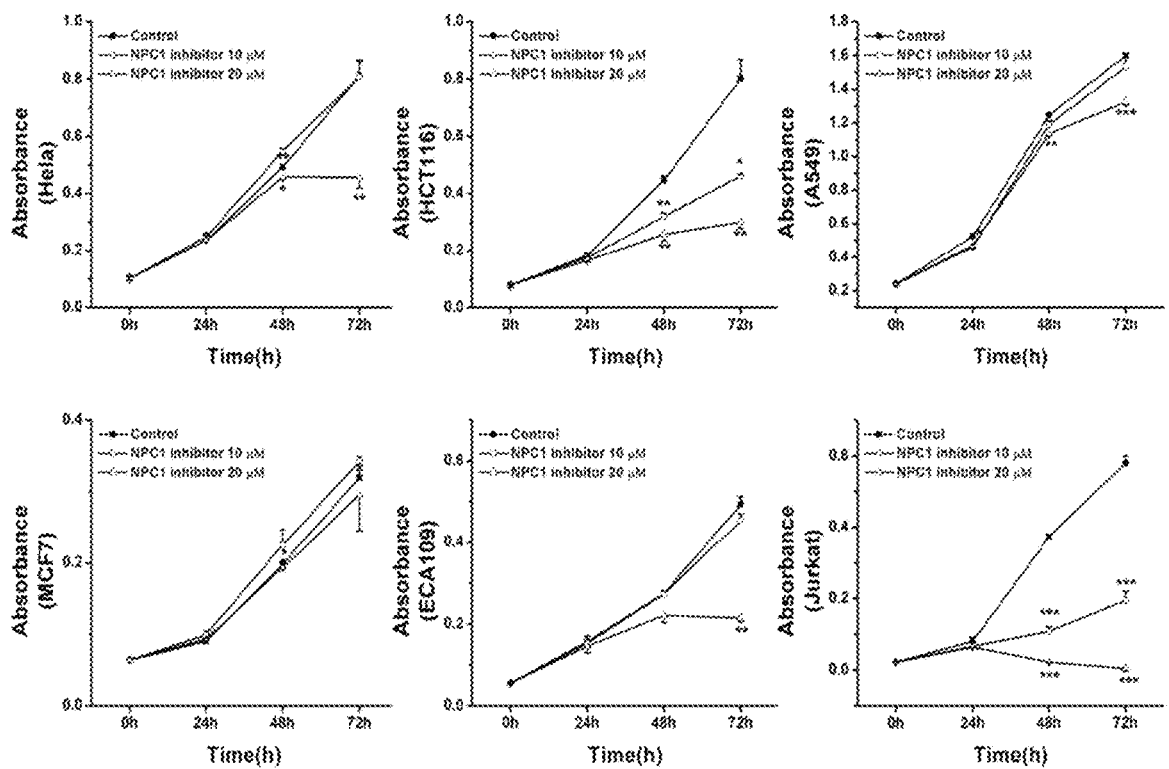
FIG. 4 shows the effects of NPC1 inhibitor U18666A on the proliferation of other common tumor cell lines. The results showed that NPC1 inhibitor U18666A significantly inhibited the proliferation of tumor cells (cervical cancer cell line Hela, colon cancer cell line HCT116, non-small cell lung cancer cell line A549, breast cancer cell line MCF7, esophageal cancer cell line ECA109 and leukemia cell line Jurkat). *$P<0.05$, $P<0.01$, *$P<0.001$.

The results showed that NPC1 inhibitor U18666A significantly inhibited the proliferation of common cancer cell lines (cervical cancer cell line Hela, colon cancer cell line HCT116, non-small cell lung cancer cell line A549, breast cancer cell line MCF7, esophageal cancer cell line ECA109 and leukemia cell line Jurkat) (FIG. 4). This shows that NPC1 can significantly inhibit the proliferation of cancer cell lines, suggesting that NPC1 may be used as a target for cancer treatment.

Example 5. In Vivo Inhibition Results of NPC1 Inhibitor in the Treatment of HepG2 Cells Orthotopic Transplantation Tumors 1. Experimental Materials 1.1 Pharmaceutical Preparations Sodium chloride injection (batch number: 1704143102) was purchased from Shijiazhuang No. 4 Pharmaceutical.

Carboxymethyl cellulose sodium (CMC-Na) (batch number: F20100420) was purchased from Sinopharm Chemical Reagent Co., Ltd.

TWEEN 80 (batch number: 040731) was purchased from BICR.

DMSO (batch number: 127790025-ACROS) was purchased from Innochem.

Anesthetic:
Ketamine hydrochloride injection (appearance: colorless and clear liquid, 50 mg/ml, batch number: 1505244) was purchased from Fujian Gutian Pharma Co., Ltd.
Xylazine (appearance: white powder, batch number: #SLBF-4886V) was purchased from Sigma, United States.

1.2 Drug Formulation

Sodium chloride injection was preheated to 37 C, and 4 mg U18666A was weighed and dissolved in 2 ml of the preheated sodium chloride injection.

Anesthetic preparation: xylazine was weighed and dissolved in sodium chloride injection and prepared into a 20 mg/ml solution for later use. Each 10 ml solution contained 1 ml ketamine hydrochloride injection (50 mg/ml).

1.3 Experimental Animals

A total of 30 female Nu/Nu nude mice aged 5-7 weeks and weighing 18.0-21.0 g were purchased from Beijing Vital River Laboratory Animal Technology Co., Ltd., animal certificate was SCXK (JING)-2015-0001. The test animals were kept in sterile independent ventilation cages (IVC), with 5-6 mice per cage. The litter was corncob litter sterilized by $^{60}$Co radiation, with a particle size of 4-6 mm. The animals were fed with sterilized feed specially formulated for mice and were given pure water to drink freely. The temperature in the animal laboratory was maintained at about 25° C., the relative humidity was maintained at 40-70%, and the daily light was 12 hours.

2 Experimental Methods

2.1 Cell Line

Human liver cancer cell line HepG2 was purchased from Union Cell Bank (Cell Center, Institute of Basic Medical Sciences, Chinese Academy of Medical Sciences & Peking Union Medical College).

2.2 Cell Culture

Cells were cultured in DMEM cell culture medium containing 10% fetal bovine serum (supplemented with penicillin and streptomycin (100 μl/ml each)), placed in a 37° C., 5% $CO_2$ incubator, and the medium was changed every 1-2 days. The cells were digested with 0.25% trypsin for passage, centrifuged at 1000 r/min for 5 minutes, the supernatant was discarded and fresh medium was added to passage the cells.

2.3 Preservation of Subcutaneous Transplantation Tumor Model

The cells in the logarithmic growth phase were digested with trypsin and collected, washed and resuspended with normal saline, so that the final cell concentration was about $1 \times 10^7$ cells/ml suspension. 0.2 ml of tumor cell suspension was injected under the skin of the right forelimb axillary in nude mice, and the tumor-bearing nude mice were established for passage and preservation.

2.4 Establishment of Orthotopic Tumor Model

When the subcutaneous tumor volume of the nude mice for preservation grew to 1000-1500 $mm^3$, tumors were removed and cut into tumor blocks of about 1.0 $mm^3$ for use under aseptic conditions. The nude mice to be operated were anesthetized and fixed on the operating table, and the abdominal skin was disinfected. An incision of about 1 cm was made in the upper right abdomen to expose the liver and the animal was covered with surgical drapes. The prepared tumor block was put into a special inoculation trocar, the tumor block was implanted into the liver with the trocar, and the bleeding wound was treated with a sterile cotton swab to stop bleeding. Then the liver after the operation was put back into the abdominal cavity of the mouse, and the abdominal muscles and skin of the incision were sutured sequentially with No. 4/0 surgical suture needle.

3. Experiment Grouping and Treatment Scheme

The experiment preset model control group and U18666A group.

Model animals were examined by B-ultrasound 3 weeks after operation, and grouped randomly according to B-ultrasound results. The test drug U18666A was administered intraperitoneally, once a day.

After the experiment, the animals were sacrificed by cervical dislocation. The liver was dissected, and the tumors visible to the naked eye were removed and weighed. All dissected tissues were preserved in a 4% formaldehyde solution for routine pathological examination.

4. Data Processing

Data were represented as $\bar{x} \pm SD$; Tumor growth inhibition rate=(tumor weight in the control group−tumor weight in the administration group)/tumor weight in the control group× 100%. All analyses were completed with GrghPad Prism software, and $P<0.05$ was considered to indicate a significant difference.

Figure 5:
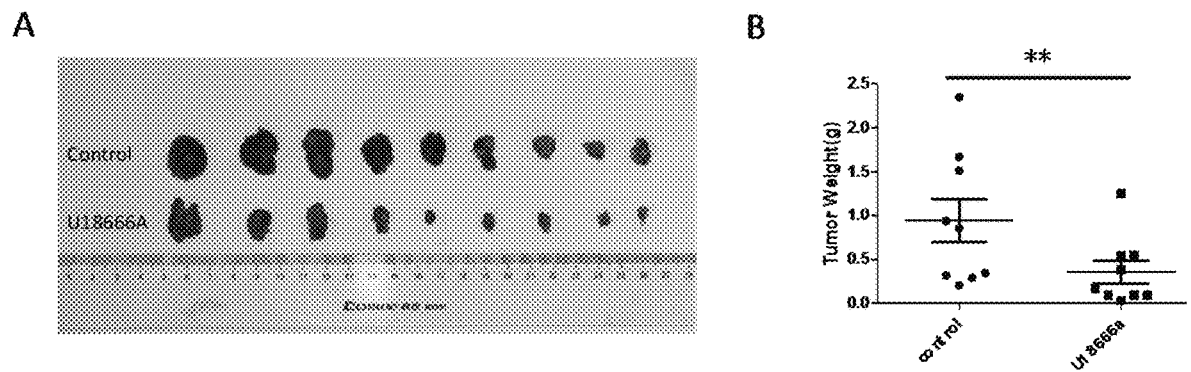
FIG. 5 shows the therapeutic effect of U18666A on the growth of liver orthotopic transplantation tumors in nude mice bearing human hepatocarcinoma HepG2 cells. Panel A shows the list of tumors dissected after 23 days of treatment in the drug treatment group (U18666a, i.p., 20 mg/kg, once a day) and the control group and a statistical analysis of tumor weights (Panel B). See Table 3 and Table 4 for specific data. Data were represented as x̄±SD, using unpaired Mann-Whitney test. **P<0.01.

The specific results are shown in Table 3, Table 4 and FIG. 5.

TABLE 3

Therapeutic effect of U18666A on the growth of liver orthotopic transplantation tumors in nude mice bearing human hepatocarcinoma HepG2 cells

| Group | Administration mode | Number of animals | | Average weight (g) | | Tumor weight (g) | Tumor growth inhibition rate (%) |
|---|---|---|---|---|---|---|---|
| | | Begining | End | Begining | End | | |
| Control group | — | 9 | 9 | 23.72 ± 1.31 | 22.60 ± 3.69 | 0.9434 ± 0.7831 | — |

TABLE 3-continued

Therapeutic effect of U18666A on the growth of liver orthotopic transplantation tumors in nude mice bearing human hepatocarcinoma HepG2 cells

| Group | Administration mode | Number of animals Begining | Number of animals End | Average weight (g) Begining | Average weight (g) End | Tumor weight (g) | Tumor growth inhibition rate (%) |
|---|---|---|---|---|---|---|---|
| U18666A | Pi. | 9 | 9 | 23.74 ± 0.86 | 23.34 ± 2.29 | 0.3574 ± 0.3914 | 62.1 |

TABLE 4

Weights of liver orthotopic transplantation tumors in nude mice bearing human hepatocarcinoma HepG2 cells in the control group and U18666A group

| Group | Tumor weight (g) | | | | | | | |
|---|---|---|---|---|---|---|---|---|
| Control | 0.2056 | 0.2906 | 0.3204 | 0.3453 | 0.8541 | 0.9373 | 1.5156 | 1.6715 | 2.3498 |
| U18666A | 0.0333 | 0.0916 | 0.0957 | 0.0958 | 0.1653 | 0.3852 | 0.5450 | 0.5512 | 1.2533 |

Example 6. Mechanism of U18666A Inhibiting Tumor Cell Growth

NPC1 knockdown and U18666A will significantly reduce the free cholesterol on the cell membrane, which will affect the expression of some receptor molecules that are located on the plasma membrane and whose location is affected by the plasma membrane cholesterol content. The IL6-IL6R-STAT3 signaling pathway is closely related to the survival, apoptosis and drug resistance of tumor cells. IL6R, which connects intracellular and extracellular signals, is located in the plasma membrane. When the plasma membrane cholesterol content is down-regulated, IL6R is shed from the plasma membrane, resulting in blocking the activation of intracellular STAT3 signaling pathway.

Reagents: Cholesterol Cell-Based Detection Assay Kit (No10009779) was purchased from Cayman. Human sIL6R ELISA kit (BMS214) was purchased from ebioscience. The relevant experiments were conducted according to the instructions.

STAT3-Y705 (EP2147Y) antibody was purchased from Abcam.

Figure 6:
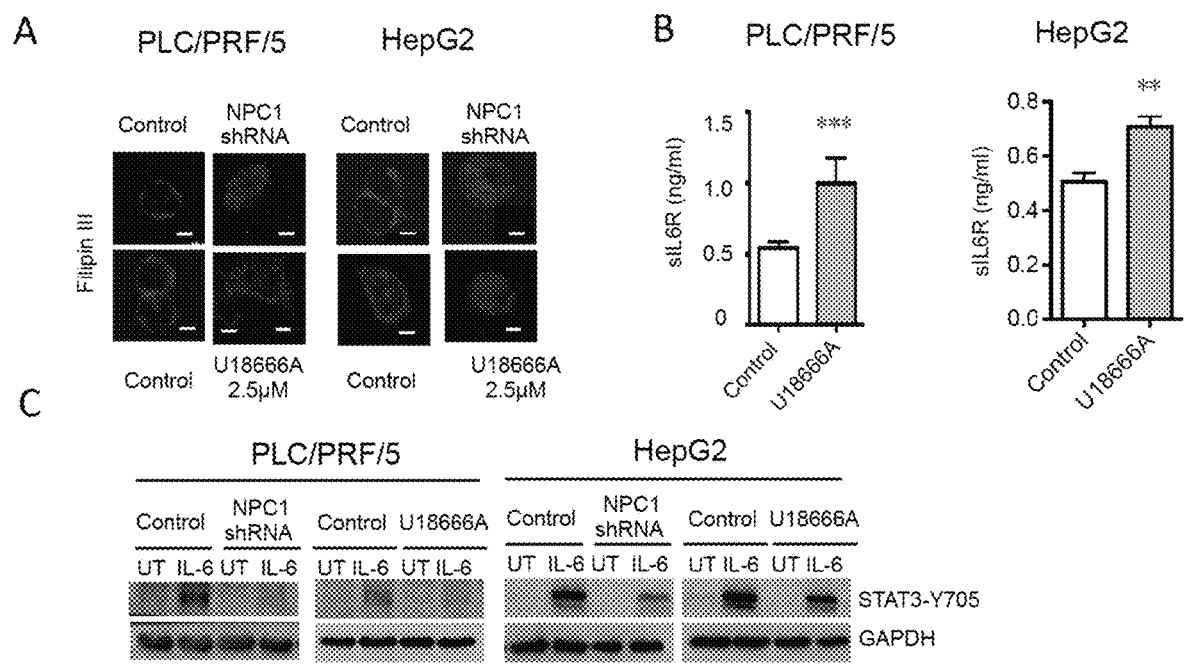
FIG. 6 shows the mechanism diagram of U18666A inhibiting tumor cell growth. Panel A: Filipin III-based cholesterol staining experiment results showed that NPC1 knockdown and drug (U18666A) could reduce cholesterol on the surface of the plasma membrane. Panel B: NPC1 inhibitor (U18666A) could increase the shedding of IL6R on the cell surface. Panel B: IL6 stimulation failed to activate the STAT3 signaling pathway of NPC1 knockdown cells and inhibitor (U18666A)-treated cells. It is suggested that NPC1 knockdown and inhibitor (U18666A) can inhibit the IL6-STAT3 signaling pathway, which plays an important role in the occurrence and development of liver cancer, by shedding the IL6R receptor on the surface of the plasma membrane. Unpaired Mann-Whitney test, *P<0.05, P<0.01, *P<0.001.

The specific results are shown in FIG. 6.

It can be seen from FIG. 6 that U18666A inhibited the activation of the STAT3 signaling pathway by down-regulating the plasma membrane IL6R abundance to inhibit tumor cell growth. FIG. 6, panel A: NPC1 knockdown or U18666A treatment significantly down-regulated plasma membrane cholesterol. FIG. 6, panel B: U18666A treatment of cells resulted in increased shedding of IL6R receptor on the cell membrane. FIG. 6, panel C: the activation of STAT3 signaling pathway was blocked after NPC1 knockdown or U18666A treatment.

The invention claimed is:

1. A method for screening a human subject for treatment for hepatocellular carcinoma (HCC) comprising: obtaining a biological sample consisting of blood or liver tissue from the human subject; subjecting the biological sample to an enzyme-linked immunosorbent assay (ELISA), wherein the ELISA is configured for determining a protein concentration of a human Niemann-Pick C1 (NPC1); and evaluating the protein concentration of the human NPC1 in the biological sample, wherein a combination of a protein concentration of >3.28 ng/ml and an area under the curve (AUC) value of >0.87 indicates the presence of the hepatocellular carcinoma: and treating the human subject with an NPC1 inhibitor selected from the group consisting of U18666A, U18666A derivatives, U18666A analogs, and combinations thereof, and/or treating the human subject with an anticancer drug selected from the group consisting of adriamycin, vincristine, paclitaxel, cisplatin, carboplatin, 5-FU, and combination thereof.

2. A method for screening a human subject under treatment for hepatitis or liver cirrhosis for HCC comprising treating the human subject with a current dosage of a composition of a NPC1 inhibitor selected from the group consisting of U18666A, U18666A derivatives, U18666A analogs, and combinations thereof and/or an anti-cancer drug selected from the group consisting of adriamycin, vincristine, paclitaxel, cisplatin, carboplatin, 5-FU, and combinations thereof; and obtaining a biological sample consisting of blood or liver tissue from the human subject; subjecting the biological sample to an ELISA, wherein the ELISA is configured for determining a protein concentration of a human NPC1; and evaluating the protein concentration of the human NPC1 in the biological sample, wherein a combination of a protein concentration of >5.44 ng/ml and an AUC value of >0.75 indicates the presence of the hepatocellular carcinoma; and when the evaluation indicates a reduction in the presence of the hepatocellular carcinoma in the biological sample, determining an adjustment, if any, to the current dosage of the composition of the NPC1 inhibitor and/or the anti-cancer drug to obtain a continuing dosage; and resuming the process of treating the human subject using the continuing dosage of the NPC1 inhibitor and/or the anti-cancer drug.

3. A method for evaluating the progress of a human subject under treatment for HCC comprising: treating the human subject with a NPC1 inhibitor selected from the group consisting of U18666A, U18666A derivatives, U18666A analogs, and combinations thereof, and/or treating the human subject with an anti-cancer drug selected from the group consisting of adriamycin, vincristine, paclitaxel, cisplatin, carboplatin, 5-FU, and combination thereof; obtaining a NPC1 protein from biological samples from the human subject over an evaluation period, wherein the biological samples consist of blood or liver tissue from the human subject; subjecting the NPC1 protein from the biological samples to an ELISA, wherein the ELISA is configured for determining a protein concentration of a human NPC1; and evaluating the protein concentration of the human NPC1 in the biological samples, wherein a combination of a protein concentration of >3.28 ng/ml and an AUC value of >0.87 indicates the continuing presence of the hepatocellular carcinoma, and wherein a combination of the protein concentration of <3.28 ng/ml and an AUC value of <0.87 indicates a reduction of the hepatocellular carcinoma; and when the evaluation indicates an increasing presence of the hepatocellular carcinoma in the human subject, increasing a dosage of the NPC1 inhibitor and/or anti-cancer drug and continuing treating the human subject with the NPC1 inhibitor and/or the anti-cancer drug.

4. A method for determining a prognosis for a human subject suspected of having HCC comprising: obtaining a biological sample consisting of blood or liver tissue from the human subject; subjecting the biological sample to an ELISA, wherein the ELISA is configured for determining a protein concentration of a human NPC1; and evaluating the protein concentration of the human NPC1 in the biological sample, wherein a combination of the protein concentration and an AUC value are used in determining a prognosis for the subject; when the evaluation indicates the presence of hepatocellular carcinoma in the human subject; and treating the human subject with an NPC1 inhibitor selected from the group consisting of U18666A, U18666A derivatives, U18666A analogs, and combinations thereof, and/or an anti-cancer drug selected from the group consisting of adriamycin, vincristine, paclitaxel, cisplatin, carboplatin, 5-FU, and combinations thereof; then, repeating the evaluation of the human subject after a treatment period; and providing a prognosis based on a collection of results from prior treatment of human subjects.

* * * * *